United States Patent
Alexander et al.

(10) Patent No.: US 6,555,724 B2
(45) Date of Patent: Apr. 29, 2003

(54) HYDROCARBON DEHYDROGENATION CATALYST AND PROCESS

(75) Inventors: Bruce D. Alexander, Lombard, IL (US); George A. Huff, Jr., Naperville, IL (US)

(73) Assignee: BP Corporation North America Inc., Warrenville, IL (US)

( * ) Notice: Subject to any disclaimer, the term of this patent is extended or adjusted under 35 U.S.C. 154(b) by 0 days.

(21) Appl. No.: 09/760,968

(22) Filed: Jan. 16, 2001

(65) Prior Publication Data

US 2002/0004624 A1 Jan. 10, 2002

Related U.S. Application Data

(60) Provisional application No. 60/178,043, filed on Jul. 24, 2000.

(51) Int. Cl.$^7$ .............................. C07C 5/333

(52) U.S. Cl. .................. 585/661; 585/660; 585/662; 585/663

(58) Field of Search .................. 585/660, 661, 585/662, 663

(56) References Cited

U.S. PATENT DOCUMENTS

| | | | | |
|---|---|---|---|---|
| 4,433,190 A | * | 2/1984 | Sikkenga et al. | 502/202 |
| 5,114,565 A | | 5/1992 | Zones et al. | 208/138 |
| 5,208,201 A | | 5/1993 | Barri et al. | 502/253 |

* cited by examiner

*Primary Examiner*—Thuan D. Dang
(74) *Attorney, Agent, or Firm*—James R. Henes

(57) ABSTRACT

A catalyst and a process employing such catalyst for the dehydrogenation of paraffinic hydrocarbons are disclosed, wherein the catalyst comprises a platinum group metal component, a zinc component and a magnesium component on a support comprising ZSM or borosilicate.

6 Claims, No Drawings

HYDROCARBON DEHYDROGENATION CATALYST AND PROCESS

REFERENCE TO RELATED APPLICATIONS

This application claims the benefit of the filing date of U.S. Provisional Application Ser. No. 60/178,043, filed Jan. 24, 2000.

BACKGROUND OF THE INVENTION

This invention relates to a process and catalyst for the dehydrogenation of hydrocarbons. More particularly, this invention relates to a catalyst and process for the dehydrogenation of paraffinic hydrocarbon utilizing a catalyst comprising a platinum group metal component, a zinc component and a magnesium component on a support component comprising ZSM or borosilicate, useful for the production of chemical industry feedstocks.

Propylene, also termed propene, is a commercially valuable feedstock employed in the manufacture of polypropylene, acrylonitrile, and propylene oxide. More than ninety-five percent of propylene is presently produced as a byproduct of olefins cracking and recovered. Propane dehydrogenation (hereinafter referred to as "PDH") is an alternative route for producing propylene. However, previously known PDH processes have been hampered by relatively low chemical conversion of propane.

Processes for dehydrogenating paraffins in the presence of hydrogen and a catalyst comprising a platinum group metal on an amorphous alumina support have been disclosed in the art.

For example, U.S. Pat. Nos. 4,190,521, 4,374,046, and 4,458,098 to Antos disclose a catalyst comprising a platinum group component, nickel, and a zinc on a porous carrier material such as alumina for dehydrogenating paraffinic hydrocarbon.

U.S. Pat. No. 4,438,288 to Imai et al. discloses a dehydrogenation process using a catalyst comprising a platinum group component, an alkali or alkaline earth component, and optionally a Group IV component such as tin, on a porous support material such as alumina. The properties and characteristics of the catalyst generally necessitate periodic catalyst regeneration in the presence of a halogen.

Processes for dehydrogenating paraffins in the presence of hydrogen and a catalyst comprising a platinum group metal on an aluminosilicate or silicalite molecular sieve support have also been disclosed in the art.

For example, U.S. Pat. Nos. 4,665,267 and 4,795,732 to Barn and U.S. Pat. Nos. 5,208,201, and 5,126,502 to Barn et al. disclose processes for dehydrogenation of 2 to 30 paraffins using a catalyst comprising zinc and a platinum group metal on a support having the silicalite structure wherein the framework of the structure consists essentially of silicon and oxygen atoms or of silicon, zinc, and oxygen atoms. The catalyst is generally formed such that it is substantially free of all alkali or alkaline earth metals.

U.S. Pat. No. 4,727,216 to Miller discloses a process for dehydrogenating isobutane in the presence of a sulfur-containing gas and a dehydrogenation catalyst. The dehydrogenation catalyst comprises a sulfided L zeolite containing from 8–10% by weight barium, from 0.6–1.0% platinum, and tin at an atomic ratio with the platinum of about 1:1. The dehydrogenation catalyst further comprises an inorganic binder selected from the group consisting of silica, alumina, and aluminosilicates.

A process for dehydrogenating paraffins in the presence of hydrogen and a catalyst comprising a platinum group metal on a non-zeolitic borosilicate molecular sieve support has been disclosed in the art.

U.S. Pat. No. 4,433,190 to Sikkenga et. al. discloses a process for dehydrogenating and isomerizing a substantially linear alkane using a dehydrogenation catalyst comprising an AMS-1B crystalline borosilicate-based catalyst composition and containing a noble metal.

U.S. Pat. No. 6,103,103 to Alexander et. al. discloses a dehydrogenation process and catalyst comprising a platinum group metal and zinc on a support comprising borosilicate and an alkali metal which provides superior dehydrogenation performance in terms of paraffin conversion, olefin selectivity, and olefin yield which is superior to that of the prior art dehydrogenation catalysts and maintains such level of superior performance for an extended period of time.

Although previous researchers have recorded many important advances, as described above, a need still exists for an improved PDH catalyst and process. Chemical manufacturers would welcome an improved PDH catalyst and process which exhibits a relatively higher chemical conversion of propane and improved stability, as compared to previously known processes and catalysts.

For purposes of the present invention, paraffin conversion and olefin selectivity shall have the following meanings and shall be calculated by mole and in accordance with the following models:

$$\text{Paraffin Conversion} = \frac{100 - \text{Mol \% } H_{2\,product} - \text{Mol \% Paraffin}_{product}}{100 - \text{Mol \% } H_{2\,feed}} \times 100$$

$$\text{Olefin Selectivity} = \frac{\text{Mol \% Olefin}_{product}}{100 - \text{Mol \% } H_{2\,product} - \text{Mol \% Paraffin}_{product}} \times 100$$

It is therefore an object of the present invention to provide a dehydrogenation process and catalyst that effectively dehydrogenate paraffinic hydrocarbon.

It is another object of the present invention to provide a dehydrogenation catalyst that resists deactivation and prolongs catalyst cycle life under dehydrogenation conditions.

Other objects appear herein.

SUMMARY OF THE INVENTION

The above objects can be achieved by providing a dehydrogenation catalyst and a process employing such catalyst for dehydrogenating a hydrocarbon having from two to about 20 carbon atoms per molecule and producing an olefinic product, wherein the catalyst comprises from about 0.01 weight percent to about 2.0 weight percent of a platinum group metal-containing component, from about 0.01 weight percent to about 15.0 weight percent of a zinc-containing component, from about 0.01 weight percent to about 5.0 weight percent of a magnesium-containing component, and a support component comprising ZSM or borosilicate having a ZSM-type structure. The process comprises contacting the aforesaid hydrocarbon with the aforesaid catalyst under dehydrogenation conditions.

The dehydrogenation catalyst and process of the present invention provide superior overall dehydrogenation properties and particularly high levels of paraffin conversion that closely approach thermodynamic equilibrium, while resisting deactivation under dehydrogenation conditions, thereby extending catalyst life.

BRIEF DESCRIPTION OF THE INVENTION

In the process of the present invention, a chargestock containing hydrocarbon having from about two to about twenty carbon atoms per molecule, preferably from about two to about six carbon atoms per molecule, and most preferably about three carbon atoms per molecule, is exposed to a catalytic composition, as described below and at effective dehydrogenation conditions. The chargestock may additionally include hydrogen, steam, carbon dioxide, carbon monoxide, or nitrogen.

In one embodiment, the process of the present invention can be employed to dehydrogenate hydrocarbon as feed for commercial chemical manufacture. Feedstocks having from 2 to 4 carbon atoms can be dehydrogenated into olefinic feedstocks for the subsequent production of polyethylene, polypropylene, polybutene, or other chemical compositions that are commonly sold in solid or liquid forms.

In a second embodiment, the process of the present invention can be employed for dehydrogenating hydrocarbon for direct or eventual upgrade to ethers such as, but not limited to, MTBE, ETBE, and TAME. Feedstocks for use with the present invention and suitable for providing etherification feedstocks will generally comprise aliphatic or alicyclic hydrocarbon having from 3 to 7 carbon atoms. The preferred feedstocks generally comprise at least 5 weight percent paraffinic hydrocarbon and more preferably at least 10 weight percent paraffinic hydrocarbon to justify the capital and operating costs to perform dehydrogenation. Since most etherification processes convert branched olefins to ethers, the feedstock to such processes often must be isomerized prior to etherification. The process of the present invention can effectively dehydrogenate paraffins as well as normal paraffins, thereby providing the flexibility to incorporate the process upstream, downstream or concurrent with an isomerization step.

In a third embodiment, the process of the present invention can be employed for dehydrogenating hydrocarbon for improving gasoline research and/or motor octane. Generally, olefinic hydrocarbon boiling in the gasoline or naphtha boiling point temperature range has a higher research and motor octane than its paraffinic counterparts. At least a portion of such feedstocks will generally comprise paraffinic hydrocarbon having from 4 to 12 carbon atoms and the paraffinic hydrocarbon can be normal, branched, or a combination thereof.

In still another embodiment, the process of the present invention can be employed to dehydrogenate hydrocarbon for feed to a petroleum refinery alkylation process. Feedstocks suitable for dehydrogenation in accordance with the present invention and for providing feedstock for an alkylation unit preferably comprise paraffinic hydrocarbons having from 3 to 6 carbon atoms and more preferably from 3 to 5 carbon atoms. The paraffinic fraction of the feedstock can be normal, branched, or a combination thereof.

The above feedstocks can be employed in the process of the present invention neat or can be combined with recycled portions of the product stream from the dehydrogenation process. Similarly, combinations of the above-described feedstocks can be employed in the process of the present invention and the products subsequently fractionated to individual product pools. The process of the present invention can also be operated in "blocked out" mode where only one feedstock is processed through the facility at any one time. Other feedstock combinations and methods to adapt the process of the present invention to individual needs will be known to those skilled in the art.

The catalyst of the present invention comprises a dehydrogenation catalyst comprising a platinum group metal-containing component, a zinc-containing component, and a magnesium-containing component on a support component comprising ZSM or a borosilicate molecular sieve. The molecular sieve-containing support can also comprise a refractory inorganic oxide binder.

The zinc-containing component can be present on the catalyst in its elemental form or as its oxide, sulfide, or mixtures thereof. The zinc-containing component is generally present in the dehydrogenation catalyst in an amount ranging from about 0.01 weight percent to about 15.0 weight percent, more preferably from about 0.1 weight percent to about 5.0 weight percent, and most preferably from about 1.0 weight percent to about 1.5 weight percent, based on the total weight of the dehydrogenation catalyst and calculated as elemental zinc.

The platinum group metal-containing component can include one or more of the platinum group metals, preferably platinum or palladium, and more preferably platinum for best results. The platinum group metal-containing component can be present in the dehydrogenation catalyst in the elemental form or as the oxide, sulfide, or mixtures thereof of the platinum group metal. The platinum group metals are cumulatively present in an amount ranging from about 0.01 weight percent to about 2.0 weight percent, more preferably from about 0.1 weight percent to about 1.0 weight percent, and most preferably from about 0.25 weight percent to about 0.5 weight percent, based on the total weight of the catalyst and calculated as the elemental platinum group metal or metals present.

Catalyst dehydrogenation metals concentrations outside of the above-described levels for the zinc-containing and cumulative platinum group metal-containing components are generally less economic. Higher metals concentrations can require more total dehydrogenation metal component due to reduced dispersion and hydrocarbon/catalyst contact. Lower metals concentrations can result in increased support material requirements, catalyst handling, transportation, and capital costs.

The zinc and platinum group dehydrogenation metal components can be deposed or incorporated upon the support component by impregnation employing heat-decomposable salts of the zinc and platinum group metals or through other methods known to those skilled in the art such as ion-exchange, with impregnation methods being preferred. The zinc-containing and platinum group metal-containing components can be impregnated onto the support separately, or can be co-impregnated onto the support. Suitable aqueous impregnation solutions include, but are not limited to, zinc nitrate, zinc chloride, chloroplatinic acid, palladium chloride, tetraamine palladium chloride, and tetraamine platinum chloride.

Impregnation using an impregnation solution comprising zinc nitrate and tetraamine platinum chloride can be performed by precalcining the dehydrogenation support component, in the form of a powder, pellets, extrudates, or spheres and determining the amount of water that must be added to wet all of the material. The zinc nitrate and tetraamine platinum chloride are then dissolved in the calculated amount of water, and the solution is added to the support in a manner such that the solution completely saturates the support. The zinc nitrate and tetraamine platinum chloride are added in a manner such that the aqueous solution contains the total amount of elemental zinc and platinum to be deposited on the given mass of support.

Impregnation can be performed for each metal separately, including an intervening drying step between impregnations, or as a single co-impregnation step. The saturated support is then generally separated, drained, and dried in preparation for calcining. Commercially, draining volumes can be reduced in order to reduce zinc and platinum losses and waste water handling costs by providing less than the full amount of aqueous solution (such as from 90% to 100% by volume of aqueous solution) necessary to saturate all of the support. Calcination generally is performed at a temperature of from about 600° F. to about 1,202° F. (315° C. to about 650° C.), or more preferably from about 700° F. to about 1,067° F. (371° C. to about 575° C.) for best results.

It has been found that combining zinc-containing and platinum group metal-containing components in accordance with the present invention provides substantially improved dehydrogenation stability resulting in longer catalyst cycles between regenerations and extended overall catalyst life before replacement. For the best results, the zinc-containing and platinum group metal-containing components can be added to the catalyst of the present invention in zinc to platinum group weight ratios extending from 10:1 to 1:10, preferably from 7:1 to 1:7, and most preferably from 7:1 to 1:1 calculated on the basis of elemental zinc and the elemental platinum group metal.

It has also been found that during dehydrogenation operation in accordance with the present invention, post-analysis of the catalyst after significant hours on stream can show significant reductions in the concentration of the zinc-containing component on the catalyst to levels as low as 50 percent, 25 percent, and even 15 percent of the level of the originally impregnated catalyst. This is believed to be due to volatilization of the impregnated zinc-containing component during dehydrogenation operations where operating temperatures can often exceed 1000° F. While the concentration of the zinc-containing component and therefore the zinc to platinum ratio tend to be reduced with on stream time, the catalyst performance is generally not substantially affected. Zinc volatilization can be managed by post incorporation of zinc after a regeneration cycle or by addition of a Group IVB metal such as zirconium during initial catalyst formulation.

It has been unexpectedly found that the presence on the catalyst of the present invention of a magnesium-containing component as a third metal-containing component in the dehydrogenation process of the present invention is essential in order to maximize catalyst stability and results in higher olefin yields and superior dehydrogenation performance. The dehydrogenation catalyst support component comprises a particularly targeted concentration of the magnesium-containing component, calculated as a percentage by weight of the dehydrogenation catalyst. The concentration of the magnesium-containing component of the dehydrogenation catalyst of the present invention ranges from about 0.01 weight percent to about 5.0 weight percent, more preferably from about 0.1 weight percent to about 1.5 weight percent, and most preferably from about 0.3 weight percent to about 0.5 weight percent, calculated as a percentage of the total catalyst and calculated as elemental magnesium.

Addition of magnesium can be accomplished by impregnation with heat-decomposable salts of magnesium, such as magnesium nitrate or magnesium acetate, or by other methods known to those skilled in the art such as ion-exchange, with impregnation being preferred. Impregnation can begin by precalcining the support component in preparation for using incipient wetness techniques. Under conventional incipient wetness techniques, a determination is generally made as to the amount of water required to saturate and fill the pores of the support component. A solution is then prepared utilizing the predetermined amount of water and a sufficient amount of the magnesium salt to provide a dehydrogenation catalyst having the desired concentration of magnesium. The impregnated support component is then separated, drained, and dried in preparation for calcining. Calcination is generally performed at a temperature ranging from about 600° F. to about 1,202° F., and preferably from about 700° F. to about 1067° F.

The dehydrogenation catalyst in accordance with the present invention can and generally does comprise various binders or matrix materials depending on the intended process use. The base catalyst can be combined with active or inactive materials, synthetic or naturally-occurring zeolites, as well as inorganic or organic materials which would be useful for binding the borosilicate. Well-known materials include silica, silica-alumina, alumina, alumina sols, hydrated aluminas, clays such as bentonite or kaolin, or other binders known in the art. Silica is the preferred binder for use with the dehydrogenation catalyst of the present invention. Preferably the silica comprises less than about 250 parts per million of aluminum and less than about 250 parts per million of sodium, based on the total weight of the catalyst. Dehydrogenation catalysts in accordance with the present invention and having silica binders are generally preferable to alternative binders in that they do not generally affect overall catalyst acidity in contradistinction to binders such as alumina and other metal oxides commonly used in catalysis.

The ZSM or borosilicate molecular sieve component is generally present in the dehydrogenation catalyst of the present invention in an amount ranging from about 5.0 weight percent to about 98.0 weight percent, preferably from about 20.0 weight percent to about 80.0 weight percent, and more preferably from about 40.0 weight percent to about 60.0 weight percent for best results, with the balance being made up of the mteal components and the binder, if any employed. Crystalline ZSM or borosilicate molecular sieve component concentrations as a percentage of the dehydrogenation catalyst, in a range of from about 40.0 weight percent to about 60.0 weight percent, are particularly preferred because it has been found that these levels promote an optimum balance of paraffin conversion and olefin selectivity for producing maximum volume yields of the desired olefins. Higher percentages of the ZSM or borosilicate molecular sieve component can result in a softer and less attrition resistant dehydrogenation catalyst which can reduce catalyst life and increase catalyst costs. Lower percentages of the ZSM or borosilicate molecular sieve component can result in larger catalytic reactor size requirements. Preferably borosilicate is the molecular sieve employed.

Methods for dispersing the base catalyst comprising the borosilicate (or ZSM) molecular sieve and dehydrogenation metal components in accordance with the present invention within a refractory inorganic oxide matrix component are generally well-known to persons skilled in the art. A preferred method is to blend the base catalyst component, preferably in a finely divided form, into a sol, hydrosol, or hydrogel of an inorganic oxide, and then add a getting medium such as ammonium hydroxide to the blend with stirring to produce a gel. The resulting gel can be dried, dimensionally formed if desired, and calcined. Drying is preferably conducted in air at a temperature of about 80° F. to about 350° F. (about 27° C. to about 177° C.) for a period of several seconds to several hours. Calcination is preferably conducted by heating in air at about 932° F. to about 1202° F. (about 500° C. to about 650° C.) for a period of time ranging from about 0.5 hours to about 16 hours. Another suitable method for preparing a dispersion of a base catalyst in a refractory inorganic oxide matrix component is to dry blend particles of each, preferably in finely divided form, and then to dimensionally form the dispersion if desired.

The preferred crystalline borosilicate molecular sieves are of the AMS type and have the following composition in terms of mole ratios of oxides.

$$(0.9\pm0.2)M_{2/n}O:B_2O_3:ySiO_2:zH_2O$$

wherein M is at least one cation, n is the valence of the cation, y is between about 4 and about 600 and z is between 0 and about 160, and provide an X-ray diffraction pattern comprising the following X-ray lines and assigned strengths:

TABLE A

| d-spacing (angstroms) (*1) | Assigned Strength (*2) |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.05 | W-M |
| 1.99 ± 0.05 | VW-M |

Note (*1) Copper K alpha radiation
Note (*2) VW = very weak, W = weak, M = medium, MS = medium strong, VS = very strong For ease of reporting X-ray diffraction results, relative peak heights are arbitrarily assigned the values shown in Table B, below:

TABLE B

| Relative Peak Height | Assigned Strength (*2) |
|---|---|
| less than 10 | VW (very weak) |
| 10–19 | W (weak) |
| 20–39 | M (medium) |
| 40–70 | MS (medium strong) |
| greater than 70 | VS (very strong) |

The preferred borosilicate molecular sieve, by virtue of its superior stability and selectivity, is the AMS-1B type which is in the sodium form as synthesized. The original cation in the AMS-1B crystalline borosilicate molecular sieve, which usually is sodium ion, can be replaced all or in part by ion exchange with other cations including other metal ions and their amino complexes, alkylammonium ions, hydrogen ions, and mixtures thereof. Preferred replacing cations are those which render the crystalline borosilicate molecular sieve catalytically active, particularly for hydrocarbon conversion. Suitable catalytically active ions include hydrogen, metal ions of Groups IB, IIA, IIB, IIIA, VIE, and VIII (IUPAC), and ions of manganese, vanadium, chromium, uranium, and rare earth elements. The preferred form of AMS-1B is the hydrogen form, HAMS-IB, which can be prepared by ammonium exchange followed by calcination. Further details with respect to these crystalline borosilicate molecular sieves can be found in commonly assigned U.S. Pat. No. 4,269,813 to Klotz, which is herein incorporated by reference.

The AMS-1B borosilicate molecular sieve useful in this invention can be prepared by crystallizing an aqueous mixture of cation sources, an oxide of boron, an oxide of silicon, and an organic template compound, at a controlled pH. Typically, the mole ratios of the various reactants can be varied to produce the crystalline borosilicate molecular sieve of this invention. Specifically, the mole ratios of the initial reactant concentrations are indicated below:

|  | Broad | Preferred | Most Preferred |
|---|---|---|---|
| $SiO_2/B_2O_3$ | 5–400 | 10–150 | 10–80 |
| $R_2O^+/[R_2O^+ + M_{2/n}O]$ | 0.1–1.0 | 0.2–0.97 | 0.3–0.97 |
| $OH^-/SiO_2$ | 0.01–11 | 0.1–2 | 0.1–1 | wherein R is an organic compound and M is at least one cation having a valence n, such as an alkali metal or an alkaline earth metal cation. By regulation of the quantity of boron (represented as $B_2O_3$) in the reaction mixture, it is possible to vary the $SiO_2$ molar ratio in the final product.

More specifically, the material useful in the present invention is prepared by mixing a cation source compound, a boron oxide source, and an organic template compound in water (preferably distilled or deionized). The order of addition is generally not critical although a typical procedure is to dissolve sodium hydroxide and boric acid in water and then add the template compound. Generally, after adjusting the pH, the silicon oxide compound is added, with intensive mixing, such as that performed in a Waring blender. After the pH is checked and adjusted if necessary, the resulting slurry is transferred to a closed crystallization vessel for a suitable time. After crystallization, the resulting crystalline product can be filtered, washed with water, dried, and calcined.

During preparation, acidic conditions should be avoided. When alkali metal hydroxides are used, the values of the ratio of $OH^-/SiO_2$ shown above should furnish a pH of the system that broadly falls within the range of about 9 to about 13.5. Advantageously, the pH of the reaction system falls within the range of about 10.5 to about 11.5 and more preferably between about 10.8 and about 11.2 for best results.

Examples of oxides of silicon useful in this invention include silicic acid, sodium silicate, tetraalkyl silicates, and Ludox, a stabilized polymer of silicic acid manufactured by E.I. DuPont de Nemours & Co. The silica source is preferably a low sodium content silica source containing less than 2,000 ppm sodium and more preferably less than 1000 ppm sodium, such as Ludox HS-40 which contains about 40 wt % $SiO_2$ and 0.08 wt % $Na_2O$ or Nalco 2327 which has similar specifications. The oxide of boron source is generally boric acid although equivalent species can be used such as sodium borate and other boron-containing compounds.

Cations useful in formation of AMS-1B include alkali metal and alkaline earth metal cations such as sodium, potassium, lithium, calcium, and magnesium. Ammonium cations may be used alone or in conjunction with such metal cations. Since basic conditions are required for crystallization of the molecular sieve of this invention, the source of such cation usually is a hydroxide such as sodium hydroxide. Alternatively, AMS-1B can be prepared directly in the hydrogen form by replacing such metal cation with an organic base such as ethylenediamine.

Organic templates useful in preparing AMS-1B crystalline borosilicate molecular sieves include alkylammonium cations or precursors thereof such as tetraalkylammonium compounds. A useful organic template is tetra-n-propylammonium bromide. Diamines, such as hexamethylenediamine, can also be used.

It is noted that the preferable amount of alkylammonium template compound used in the above-described preparation method is substantially less than that required to produce AMS-1B conventionally using an alkali metal cation base.

The crystalline borosilicate molecular sieve prepared by the above-described method typically contains at least 9,000 ppm boron and less than about 100 ppm sodium and is designated as HAMS-1B-3. The HAMS-1B-3 crystalline borosilicate molecular sieve has a higher boron content and a lower sodium content than crystalline borosilicate formed using conventional techniques.

In a more detailed description of a typical preparation of the borosilicate used in the catalyst and process of the present invention, suitable quantities of sodium hydroxide and boric acid ($H_3BO_3$) are dissolved in distilled or deionized water followed by addition of the organic template. The pH may be adjusted between about 11.0±0.2 using a compatible base or acid such as sodium bisulfate or sodium hydroxide. After sufficient quantities of silicic acid polymer (Ludox HS-40) are added with intensive mixing, the pH can again be checked and adjusted to a range of from about 11.0±0.2. The resulting slurry is transferred to a closed crystallization vessel and reacted usually at a pressure of at least the vapor pressure of water for a time sufficient to permit crystallization. This time period generally ranges from about 6 hours to about 20 days, typically from about 1 day to about 10 days, and preferably extends from about 5 days to about 7 days. The temperature for crystallization is generally maintained at from about 212° F. to about 482° F., preferably from about 257° F. to about 392° F., and more preferably at about 329° F. for best results. The crystallizing material can be stirred or agitated as in a rocker bomb. Preferably, the crystallization temperature is maintained below the decomposition temperature of the organic template compound. Samples of material can be removed during crystallization to check the degree of crystallization and determine the optimum crystallization time.

The crystalline material formed can be separated and recovered by well-known means such as by filtration with washing. This material can be mildly dried for anywhere from a few hours to a few days at varying temperatures, typically ranging from about 77° F. to about 392° F., to form a dry cake. The dry cake can then be crushed to a powder or to small particles and extruded, pelletized, or made into forms suitable for its intended use. Typically, materials prepared after mild drying contain the organic template compound and water of hydration with the solid mass and a subsequent activation or calcination procedure is necessary if it is desired to remove this material from the final product. Calcination is generally performed at temperatures ranging from about 500° F. to about 1562° F. and preferably from about 977° F. to about 1112° F. for best results. Extreme calcination temperatures or prolonged crystallization times may prove detrimental to the crystal structure or may destroy it. Generally, there is minimal benefit in raising the calcination temperature beyond about 1112° F. in order to remove organic material from the originally formed crystalline material. The molecular sieve material can then be dried in a forced draft oven at about 329° F. for about 16 hours prior to calcination in air in a manner such that the temperature rise does not exceed 225° F. per hour. Once a temperature of about 1000° F. is reached, calcination temperature is generally maintained for about an additional 4 to 16 hours.

The dehydrogenation process of the present invention can begin with a hydrocarbon feedstock preheating step. The feedstock can be preheated in feed/reactor effluent heat exchangers prior to entering a furnace or contacting other high temperature waste heat means for final preheating to a targeted catalytic reaction zone inlet temperature. Suitable final preheating means can include, but are not limited to, waste heat from other refinery or petrochemical processes such as a hydrocarbon steam cracker, a fluid catalytic cracking unit, a fluidized or delayed coking unit, a catalytic hydrocracker, a crude distillation unit, a catalytic reforming unit, and/or hydrotreating units found in conventional petroleum refineries.

The feedstock can be contacted with a hydrogen stream prior to, during, and/or after preheating, before the catalytic dehydrogenation reaction zone, in any one or more of the reactors in the reaction zone, or between reactors in a multiple reactor reaction zone. The addition of supplemental hydrogen in the process can reduce the rate of catalyst deactivation, resulting in reduced catalyst regeneration requirements. However, hydrogen addition may also adversely affect olefin yield by directing the reaction stoichiometrically away from dehydrogenation and toward olefin saturation.

The hydrogen stream can be pure hydrogen or can be in admixture with diluents such as low-boiling hydrocarbons, carbon monoxide, carbon dioxide, nitrogen, water, sulfur compounds, and the like. The hydrogen stream purity should be at least about 50% by volume hydrogen, preferably at least about 65% by volume hydrogen, and more preferably at least about 75% by volume hydrogen for best results. Hydrogen can be supplied from a hydrogen plant, a catalytic reforming facility, or other hydrogen-producing or hydrogen-recovery processes.

Operating conditions to be used in the dehydrogenation process of the present invention include an average catalytic reaction zone temperature of from about 482° F. to about 1300° F., preferably from about 700° F. to about 1200° F., and more preferably from about 850° F. to about 1150° F. for best results. Reaction temperatures below these ranges can result in reduced paraffin conversion and lower olefin yield. Reaction temperatures above these ranges can result in reduced olefin selectivity and lower olefin yields.

The process of the present invention generally operates at catalytic reaction zone pressures ranging from as low as substantially vacuum pressure (about 0 to about 27.6 inches of water vacuum) to about 500 psig, preferably from about vacuum pressure to about 300 psig, and more preferably from about vacuum pressure to about 100 psig for best results.

The effective hydrogen conditions preferably include a hydrogen to hydrocarbon molar ratio of preferably 0.01 to about 5, more preferably about 0.1 to about 2, and most preferably about 0.1 to about 0.5. The effective dehydrogenation conditions also preferably include a carbon dioxide to hydrocarbon molar ratio of about 0 to about 15, more preferably about 2 to about 10, and most preferably about 3 to about 10. Steam may be present in the dehydrogenation reactor in conjunction with or as a replacement of the carbon dioxide.

Hydrogen circulation rates below these ranges can result in higher catalyst deactivation rates resulting in increased energy intensive regeneration cycles. Excessively high reaction pressures increase energy and equipment costs and provide diminishing marginal benefits. Excessively high hydrogen circulation rates can also influence reaction equilibrium and drive the reaction undesirably towards reduced paraffin conversion and lower olefin yield. The presence of carbon dioxide or steam reduces the partial pressure of the hydrocarbon resulting in higher thermodynamic equilibrium conversion of the hydrocarbon feedstock.

The process of the present invention generally operates at a liquid hourly space velocity (LHSV) of from about 0.1 $hr^{-1}$ to about 50 hr$^{-1}$, more preferably from about 0.5 hr$^{-1}$ to about 25 hr$^{-1}$, and most preferably from about 1 hr$^{-1}$ to about 10 hr$^{-1}$ for best results. Feed space velocities exceeding the levels described herein generally result in a decline in paraffin conversion which overwhelms any gain in olefin selectivity, thereby resulting in lower olefin yield. Feed space velocities short of the levels described herein are generally costly in terms of capital requirements.

The dehydrogenation catalyst and process of the present invention can be retrofitted to utilize existing processes and facilities such as, but not limited to, those previously dedicated to naphtha reforming. The reaction pressure requirements are generally low and therefore, suitable reactor vessels may be located from any of several sources. A catalytic reformer may also possess furnace hardware, hydrocarbon separation, and catalyst regeneration equipment particularly synergistic to use with the process of the present invention. Catalytic reforming is also particularly suited for retrofit with the present invention in view of recent environmental mandates to produce gasolines containing lower aromatic concentrations (a fundamental product of catalytic reforming).

The reaction zone can include, but is not limited to, one or more fixed bed reactors containing the same or different catalysts, a moving column reactor and catalyst regeneration system, or a fluidized bed reactor and regenerator, with a fixed bed reactor process being preferred. The feedstock may be contacted with a catalyst or a catalyst bed in either upward, downward, or radial flow fashion with downflow being preferred. The reactants may be in the liquid phase, admixed liquid and vapor phase, or the vapor phase, with the best results obtained in the vapor phase.

Moving column reactors and regenerator systems such as those described in U.S. Pat. No. 3,647,680 to Greenwood et al. are known in the art and commonly used in processes such as catalytic reforming. The system generally comprises a vertical elongated reaction vessel comprising moving annular columns of catalyst wherein hydrocarbon is passed in out-to-in radial flow towards the center of the reaction vessel. Portions of the moving bed of catalyst are continuously directed to a regeneration system for regenerating the catalyst through combustion of coke components.

Fluidized bed reactors, which are commonly used in fluidized catalytic cracking and fluidized coking processes, fluidize the catalyst directly within the hydrocarbon feedstock, separate the catalyst from the reaction products, and direct the spent catalyst back to a regeneration zone for regeneration. The heat of reaction from the burning of coke from the catalyst generally supplies the heat requirements for sustaining the particular process reactions.

The preferred reaction zone facilities for use with the dehydrogenation process of the present invention are fixed bed reactors. It is preferred that the dehydrogenation reaction zone comprise at least two fixed bed reactors so as to facilitate on stream regeneration of the catalyst. The fixed bed reactors are generally equipped with proper manifolding to permit removal of each reactor from operation in a manner so as to provide for regeneration of the catalyst in that reactor while the other reactor or reactors sustain process operations. Fixed bed reactors in accordance with the present invention can also comprise a plurality of catalyst beds. The plurality of catalyst beds in a single fixed bed reactor can also comprise the same or different catalysts.

Since the dehydrogenation reaction is generally endothermic, interstage heating, consisting of heat transfer devices between fixed bed reactors or between catalyst beds in the same reactor shell, can be employed. Heat sources can include conventional process heaters such as one or more process furnaces or can include internally produced heat such as that produced from catalyst regeneration within a fluidized catalytic process. Heating requirements may also be met from heating sources available from other refinery process units such as from a fluid catalytic cracking process or a fluidized coker. Multiple reactor processes can provide reduced temperature endotherm per reactor shell and more effective temperature control but generally cost more in terms of capital requirements.

The dehydrogenation reaction zone effluent is generally cooled and the effluent stream is directed to a separator device such as a stripper tower where light hydrocarbons and hydrogen formed during the reaction step can be removed and directed to more appropriate hydrocarbon pools. Where the process is performed in the presence of supplemental hydrogen or sufficient internally generated hydrogen is produced, a separate hydrogen separation step can be performed upstream of and prior to light hydrocarbon separation. Some of the recovered hydrogen can be recycled back to the process while some of the hydrogen can be purged to external systems such as plant or refinery fuel. The hydrogen purge rate can be controlled to maintain minimum hydrogen purity. Recycled hydrogen can be compressed, supplemented with "make-up" hydrogen, and reinjected into the process for further dehydrogenation where supplemental hydrogen is added.

The stripper liquid effluent product is then generally conveyed to downstream processing facilities. The olefin product can be directed to an isomerization process for isomerization and thereafter directed to an ether facility for conversion, in the presence of alkanol, to an ether. Where at least a portion of the olefin from the process of the present invention is iso-olefin, the stream can be sent directly to an ether facility. Prior to direction to an ether facility, the product stream can be purified by removing unconverted paraffinic hydrocarbon from the product. This unconverted product can be recycled back to the reaction zone or further manipulated in other process Units. The olefin product can be directed to an alkylation process for reaction with soparaffin to form higher octane, lower volatility gasoline blending components. The olefin product can be directed to a chemical manufacture process for conversion to other commodity chemical products or process streams. Methods for integration of the process of the present invention with other conventional refinery or chemical plant processes or products will be generally known to those skilled in the art.

Notwithstanding the superior stability properties of the dehydrogenation catalyst of the present invention, periodic catalyst regeneration may be required depending on the severity of operation and other process parameters. It is anticipated that the catalyst utilized in the process of the present invention may require regeneration as often as once every 6 months, as often as once every 3 months, and, on occasion, as often as once or twice every month. The dehydrogenation catalyst of the present invention is particularly suited for regeneration by the oxidation or burning of catalyst deactivating carbonaceous deposits with oxygen or an oxygen-containing gas. The term "regeneration," for purposes of the present invention, shall mean the recovery of at least a portion of the molecular sieve initial activity by combusting the coke deposits on the catalyst with oxygen or an oxygen-containing gas.

The literature is replete with catalyst regeneration techniques that may be employed in the process of the present invention. Some of these regeneration techniques involve chemical methods for increasing the activity of deactivated molecular sieves. Others, including the preferred methods, relate to processes or methods for regenerating carbon (also known as coke) deactivated catalysts by the combustion of the coke with an oxygen-containing gas stream. For example, U.S. Pat. No. 2,391,327 discloses the regeneration of catalysts contaminated with carbonaceous deposits with a cyclic flow of regeneration gases. U.S. Pat. No. 3,755,961 relates to the regeneration of is coke-containing crystalline zeolite molecular sieves which have been employed in an absorptive hydrocarbon separation process. The process involves the continuous circulation of an inert gas containing a quantity of oxygen in a closed loop arrangement through the bed of molecular sieve.

The conditions and methods at which a catalyst may be regenerated by coke combustion can vary. It is typically desired to perform coke combustion at conditions of temperature, pressure, gas space velocity, etc. which are least damaging thermally to the catalyst being regenerated. It is also desired to perform the regeneration in a timely manner to reduce process down-time in the case of a fixed bed reactor system or equipment size, in the case of a continuous regeneration process.

Optimum regeneration conditions and methods are generally disclosed in the prior art as mentioned hereabove. Catalyst regeneration is typically accomplished at conditions including a temperature range of from about 550° F. to about 1300° F., a pressure range of from about 0 psig to about 300 psig, and a regeneration gas oxygen content of from about 0.1 mole percent to about 23.0 mole percent. The oxygen content of the regeneration gas is typically increased during the course of a catalyst regeneration procedure based on catalyst bed outlet temperatures, in order to regenerate the catalyst as quickly as possible while avoiding catalyst-damaging process conditions.

The preferred catalyst regeneration conditions include a temperature ranging from about 600° F. to about 1150° F., a pressure ranging from about 0 psig to about 150 psig, and a regeneration gas oxygen content of about 0.1 mole percent to about 10 mole percent for best results.

Additionally, it is important that regeneration be accomplished in the presence of an oxygen-containing gas. The oxygen-containing regeneration gas typically comprises nitrogen and carbon combustion products such as carbon monoxide and carbon dioxide, to which oxygen in the form of air has been added. However, it is possible that the oxygen can be introduced into the regeneration gas as pure oxygen, or as a mixture of oxygen diluted with another gaseous component. Air is the preferred oxygen-containing gas.

The present invention is described in further detail in connection with the following examples, it being understood that the same are for purposes of illustration and not limitation.

Demonstration Procedure

A catalyst including 0.25 weight percent platinum, 1.8 weight percent zinc, HAMS-1B, and a silica binder is impregnated with one of four catalytically active metals selected from the group consisting of sodium, potassium or magnesium. More specifically, HAMS-1B is impregnated with an aqueous solution of zinc acetate. The impregnated HAMS-1 B is dried and calcined at 1000 degrees F. in air. Platinum is added to the impregnated HAMS-1B by incipient wetness impregnation with an aqueous solution of teraamineplatinum (II) nitrate.

The platinum-containing HAMS-1B is dried at room temperature, and dispersed in an aqueous sol of commercially available fumed silica in a 60:40 sieve to matrix weight ratio to form a gel. The gel is dried in a forced air oven, and crushed to form particles having a mesh size of about 12 to about 20. Sodium, potassium or magnesium is added to the particles by incipient wetness impregnation with an aqueous solution of sodium bicarbonate, potassium bicarbonate, cesium nitrate or magnesium nitrate, respectively, to produce a promoted catalyst for testing.

One volume of the promoted catalyst is diluted with three volumes of alpha alumina having a mesh size of about 30 to about 50 mesh. The diluted catalyst is packed into a quartz reactor tube of 11 millimeters internal diameter. The reactor tube is placed in a furnace. A hydrogen gas flow of 150 cubic centimeters per minute is maintained through the reactor tube at 538 degrees C. and one atmosphere for one hour.

In Period 1, a propane flow of 15 liquid hourly space velocity per minute is maintained through the reactor tube at 538 degrees C. for 45 minutes. In Period 2, a chargestock composed of 80 mole percent propane and 20 mole percent ethylene passes through the reactor tube at 15 liquid hourly space velocity and 538 degrees C. for 45 minutes. In Period 3, a propane flow of 15 liquid hourly space velocity per minute is maintained through the reactor tube at 538 degrees C. for 45 minutes. Propane and ethylene conversion are monitored as a function of time during each Period.

One liquid hourly space velocity means that a mass of chargestock corresponding to one volume of liquid chargestock passes through one volume of the promoted catalyst, excluding alpha alumina, in one hour. For example, assuming that liquid propane has a density of 0.50 grams per cubic centimeter, 69 volumes per minute of gas at Standard Temperature and Pressure (defined as 0 degrees C. and one atmosphere, absolute) corresponds to 15 liquid hour space velocity through one volume of the promoted catalyst.

EXAMPLE 1

The Demonstration Procedure is carried out, substantially as described above, to produce a promoted catalyst for testing which includes 1.91 weight percent sodium. The propane and ethylene conversions for the promoted catalyst including 1.91 weight percent sodium are set forth in Table I, below.

EXAMPLE 2

The Demonstration Procedure is carried out, substantially as described above, to produce a promoted catalyst for testing which includes 1.96 weight percent potassium. The propane and ethylene conversions for the promoted catalyst including 1.96 weight percent potassium are set forth in Table I, below.

EXAMPLE 3

The Demonstration Procedure is carried out, substantially as described above, to produce a promoted catalyst for testing which includes 1.14 weight percent magnesium. The propane and ethylene conversions for the promoted catalyst including 1.14 weight percent magnesium are set forth in Table I, below.

TABLE I

SUMMARY OF DEMONSTRATION PROCEDURES

| Promoter | 1.91 wt % Na | 1.96 wt % K | 1.14 wt % Mg |
| --- | --- | --- | --- |
| Period 1: Propane Conversion (%)[a] | 27 | 27 | 27 |
| Period 2: Ethylene Conversion (%)[b] | 24 | 91 | 83 |

TABLE I-continued

SUMMARY OF DEMONSTRATION PROCEDURES

| Promoter | 1.91 wt % Na | 1.96 wt % K | 1.14 wt % Mg |
|---|---|---|---|
| Period 3: Propane Conversion (%) | 10 | 24 | 26 |

Note [a] Equilibrium propane conversion at reactor conditions is 27 percent
Note [b] Ethylene to conversion to ethane The data in Table I indicate that the promoted catalyst including 1.14 weight percent magnesium is the most stable at Demonstration Test conditions of the promoted catalysts described in Examples 1 through 3.

Extended Procedure

An Extended Procedure is now described which is useful in determining the stability of promoted catalysts over an extended period of time. In the Extended Test, 10 cubic centimeters of a promoted catalyst of the present invention is packed undiluted in an elongated reactor tube including a stainless steel tube of 0.74 inches internal diameter with an inner tube sleeve of 9 millimeters internal diameter. The reactor tube has a thermocouple which is installed longitudinally along the center of the reactor tube. The thermocouple is inside a thermowell which includes a one-sixteenth inch capillary tubing surrounded by a 3 millimeter outside diameter quartz jacket. The thermocouple is moved longitudinally within the thermowell to monitor temperatures at various points. The reactor tube is placed in a three zone furnace.

The reactor tube is purged with nitrogen at room temperature. A flow of hydrogen is established through the reactor tube, and the reactor tube is heated to 600 degrees C. while hydrogen flows through the reactor tube. Hydrogen flow is maintained at 600 degrees C. for one hour. A feedstock consisting of 20 mole percent hydrogen and 80 mole percent propane is charged to the reactor tube at 600 degrees C. The pressure in the reactor tube while feedstock is being charged is in the range of about zero to 5 pounds per square inch gauge. Product gas is analyzed by gas chromatography.

EXAMPLE 4

The Extended Procedure is carried out with a promoted catalyst of the present invention, which is essentially identical to the promoted catalyst including 1.14 weight percent magnesium described in Example 3, above. Time on stream at fifty or more percent propane conversion, and propylene conversion are set forth in Table II, below.

EXAMPLE 5

The Extended Procedure is carried out with a promoted catalyst of the present invention which contains exactly 0.54 weight percent magnesium, but is otherwise essentially identical to the promoted catalyst including 1.14 weight percent magnesium described in Example 3, above. Time on stream at fifty or more percent propane conversion, and propylene conversion for the 0.54 weight percent magnesium promoted catalyst are set forth in Table II, below.

EXAMPLE 6

The Extended Procedure is carried out with a promoted catalyst of the present invention which contains exactly 0.35 weight percent magnesium added by ion exchange in an aqueous solution with excess magnesium nitrate, but is otherwise essentially identical to the promoted catalyst including 1.14 weight percent magnesium described in Example 3, above. Time on stream at fifty or more percent propane conversion, and propylene conversion for the 0.35 weight percent magnesium promoted catalyst are set forth in Table II, below.

TABLE II

SUMMARY OF EXTENDED PROCEDURES

| Promoter | 1.14 wt % Mg (impregnation) | 0.54 wt % Mg (impregnation) | 0.35 wt % Mg (ion exchange) |
|---|---|---|---|
| Hours of 50% or more Propane Conversion | 15 | 200+ | 800+ |
| Propylene Selectivity (%) | 97 | 95 | 90 |

Inspection of the data presented in Table II indicates that the promoted catalyst of the present invention is a surprisingly effective catalyst for the production of propylene by dehydrogenation of propane when about 1 weight percent of magnesium, preferably about 0.5 weight percent of magnesium, and most preferably about 0.3 weight percent of magnesium is included in the total weight of the catalyst.

Other embodiments of the invention will be apparent to recovering the olefinic product. Those skilled in the art from a consideration of this specification or from practice of the invention disclosed herein. It is intended that this specification be considered as exemplary only with the true scope and spirit of the invention being indicated by the following claims.

That which is claimed is:

1. A process for dehydrogenating propane to produce propylene comprising:

contacting propane under catalytic dehydrogenation conditions with a catalyst comprising a platinum group metal-containing component, a zinc-containing component and a magnesium-containing component, at concentration levels from about 0.01 to about 2.0 weight percent, from about 0.01 to about 15.0 weight percent and from about 0.30 to about 1.14 weight percent, respectively, in each case calculated as the elemental metal and as a percentage of the total catalyst, on a support comprising ZSM or a crystalline borosilicate having a ZSM structure, to thereby produce propylene at a selectivity of at least 90%.

2. The process of claim 1 wherein the support comprises borosilicate.

3. The process of claim 2 wherein the borosilicate is HAMS-1B.

4. The process of claim 1, wherein the support comprises a refractory inorganic oxide binder.

5. The process of claim 4 wherein the binder is silica.

6. The process of claim 5 wherein the silica binder comprises less than about 250 parts per million of aluminum and less than about 250 parts per million of sodium, based on the total weight of the silica binder.

* * * * *

UNITED STATES PATENT AND TRADEMARK OFFICE
CERTIFICATE OF CORRECTION

PATENT NO.     : 6,555,724 B2
DATED          : April 29, 2003
INVENTOR(S)    : Bruce D. Alexander and George A. Huff, Jr.

It is certified that error appears in the above-identified patent and that said Letters Patent is hereby corrected as shown below:

Column 12,
Lines 40-41, "with soparaffin to form higher octane," should read -- with isoparaffin to form higher octane, --

Signed and Sealed this

Sixteenth Day of September, 2003

JAMES E. ROGAN
*Director of the United States Patent and Trademark Office*